United States Patent [19]
Hubbell et al.

[11] Patent Number: 5,820,882
[45] Date of Patent: Oct. 13, 1998

[54] BIOCOMPATIBLE MICROCAPSULES

[75] Inventors: Jeffrey A. Hubbell; Amarpreet S. Sawhney, both of Austin, Tex.

[73] Assignee: Board of Regents, The University of Texas System, Austin, Tex.

[21] Appl. No.: 336,393

[22] Filed: Nov. 10, 1994

Related U.S. Application Data

[63] Continuation of Ser. No. 598,880, Oct. 15, 1990.

[51] Int. Cl.$^6$ .............................. A61K 9/54; A61K 9/62; A61K 9/64
[52] U.S. Cl. ...................... 424/491; 424/490; 424/493; 424/497; 424/423; 424/424; 514/772.1; 514/772.2; 514/777; 514/773
[58] Field of Search .................................... 424/497, 490, 424/462, 482, 423, 424, 493, 491, 460, 461

[56] References Cited

U.S. PATENT DOCUMENTS

| | | | |
|---|---|---|---|
| 4,076,800 | 2/1978 | Marsh et al. | 424/70 |
| 4,228,031 | 10/1980 | Iwasaki et al. | 252/316 |
| 4,352,883 | 10/1982 | Lim | 435/178 |
| 4,409,331 | 10/1983 | Lim | 435/178 |
| 4,434,150 | 2/1984 | Azad et al. | 424/1.1 |
| 4,663,286 | 5/1987 | Tsang et al. | 435/178 |
| 4,806,355 | 2/1989 | Goosen et al. | 424/424 |
| 4,906,698 | 3/1990 | Kusano et al. | 525/242 |
| 4,908,392 | 3/1990 | Kusano et al. | 521/60 |
| 4,923,645 | 5/1990 | Tsang et al. | 264/4.3 |

FOREIGN PATENT DOCUMENTS

| | | |
|---|---|---|
| 0354855 | 2/1990 | European Pat. Off. . |
| 8800237 | 1/1988 | WIPO . |

OTHER PUBLICATIONS

Kiss et al., "Surface Grafting of Polyethyleneoxide Optimized by Means of OSCA"; Progr. Colloid & Polymer Sci. 74:113–119 (1987).

Bader, Robert, et al., "Watersoluble Polymers in Medicine," *Die Angewandte Makromolekulare Chemie* 123/124:457–485 (1984).

Pratten, Margaret K., and John B. Lloyd, "Micelle–forming block copolymers: Pinocytosis by macrophages and interaction with model membranes," *Makromol. Chem.* 186:725–733 (1985).

*Primary Examiner*—James M. Spear
*Attorney, Agent, or Firm*—Arnall Golden & Gregory, LLP.

[57] ABSTRACT

Biocompatible microcapsules useful for transplanting foreign material into an animal body, and the method of their production, are described, wherein the microcapsules contain an outermost layer of water soluble non-ionic polymers such as PEO to create resistance to cell adhesion on the surface of the microcapsules.

10 Claims, 5 Drawing Sheets

BIOCOMPATIBLE MICROCAPSULES

This is a continuation of co-pending application Ser. No. 07/598,880, filed on Oct. 15, 1990.

BACKGROUND

Microencapsulation of materials for transport to and/or growth within an animal is an area of research currently attracting much interest. The use of microcapsules provides the potential for such medically important procedures as treatment of insulin-dependent diabetes mellitus (IDDM) in humans through transplantation of insulin-producing cells, and timed release or long term delivery of drugs to an animal.

The microencapsulation membrane plays a critical role in the treatment of IDDM by microencapsulated islet cells, as well as treatment of other diseases with other encapsulated material. Not only must it prohibit proteins of the immune system from entering the capsule, but it must also interact with the host tissues in a biocompatible way. In this sense, biocompatibility means that the membrane will not initiate an inflammatory response and that it will not support cell adhesion and stimulate overgrowth. If overgrowth occurs, the oxygen and nutrient supply to the islets will be limited and they will die. The area of biocompatibility of microcapsules, however, has received relatively little attention.

The principle of immunoisolation is to surround the cells with a biocompatible semipermeable membrane, which allows free diffusion of nutrients, messenger compounds, cell wastes, and cell products, while isolating the cells from the host's immune system. The cells may be individual or clumped in tissue. Messenger compounds and cell products include glucose, $Ca^{2+}$, and insulin.

Two methods for the immunoisolation of cells exists: hollow-fiber devices and microencapsulation. One form of hollow-fiber devices are an artificial capillary system consisting of hollow fibers to which cells are seeded on their exteriors, and which are enclosed in a rigid chamber that is connected to the recipient as a vascular shunt. Early devices using insulin producing cells reversed diabetes for limited periods with high doses of heparin. Sun et al. (1977) Diabetes, 26:1136–39. But even with heparin, blood clot formation was a major problem. To reduce the formation of clots, which suffocated the cells, Altman et al. have seeded Amicon fibers successfully, with nearly half of the animal recipients having normal blood glucose levels for over a year. Altman et al. (1986) Diabetes, 35:625–33. However, the Amicon fibers are fragile and they have a limited surface area available for diffusion. A U-shaped ultrafiltration design developed by Reach et al. can solve the diffusion problem, but this design still suffers from the fragility of the Amicon fibers and from the formation of blood clots at the junction with the vascular system. Reach et al. (1984) Diabetes, 33:752–61.

The transplantation of microencapsulated cells or tissue can overcome the hollow-fiber associated problems of diffusion limitations and vascular complications, originally, Sun and Lim demonstrated the technique by encapsulating rat pancreatic islet cells into a membrane composed of layers of alginate, polylysine, and polyethyleneimine. Sun and Lim (1980) Science, 210:908–910. The microcapsules were injected into chemically induced diabetic rats. These microcapsules corrected the diabetic state for only 2 to 3 weeks. Gradually the technique improved. A large improvement was making the multi-layer membrane from alginate-polylysine-alginate, which is stronger and has controllable permeability parameters. Goosen et al. (1985) Biotech. and Bioengin., XXVII:146–50. King and Goosen et al. developed methods for decreasing the viscosity of the gel inside so that the tissue or cells are in a more natural environment (1987) Biotechnology Progress, 3:231–240. A further advance was making the microcapsules in a more uniform, smooth, spherical shape which improved their strength. Walter et al. Poster Group H.

With these changes, Sun et al. have transplanted rat islets of Langerhans into chemically induced diabetic rats which have reversed the diabetic state for up to 780 days, Sun (1987) Trans Am Soc. Artif. Intern Organs, XXXIII:787–790. In vitro studies have shown that antibodies from Type 1 human diabetic patients were not able to suppress encapsulated cells, Darquy and Reach (1985) Diabetologia, 28:776–80. Therefore, it seems that microencapsulation can protect cells from antibodies. However, there are still several serious problems in regards to biocompatibility. Sun has reported finding fibroblast-like cells on the external surfaces of intact microcapsules. Sun had transplanted the microencapsulated rat islet cells into diabetic rats. Sun (1987) Trans Am. Soc. Artif. Intern Organs XXXIII:787–790. In his articles, Sun has specifically recognized the need to improve the biocompatibility of the microcapsules. Id. at 810.

Other published studies have also seen this inflammatory response to transplanted microencapsulated cells. In another study of microencapsulated rat islet cells, O'Shea and Sun found that the microcapsules that they transplanted into chemically induced diabetic mice had cell overgrowth in the range of 0–10 layers of cells. The overgrowing cells included fibroblasts, macrophage-like cells and neutrophils. There was also collagen around the capsules. O'Shea and Sun (1986) Diabetes, 35:943–946. Again, O'Shea and Sun expressly recognized that the biocompatibility of the microcapsules must be improved. Id. at 946.

The inflammatory response is not limited to transplants of islet cells. Wong and Chang have reported recovering clumped microcapsules of rat hepatocytes after they were transplanted into mice with liver failure. They found no viable cells within the clumped microcapsules, which were recovered only seven days after transplantation. Wong and Chang (1988) Biomat., Art. Cells, Art. Org., 16 (4):731–739. The cells probably died because they were cut off from nutrients when the cells grew over the semi-permeable membrane.

Current formulations for microcapsules result in algin—polycationic polymer—algin composites. The exterior of these membranes are negatively charged, due to the algin, and may have positive charges due to exposed polycation; as such they support protein adsorption and cell attachment. In general, these microcapsules become overgrown with fibroblasts and other cells. This overgrowth has many negative effects, including impairment of the functioning of the microcapsule by blocking permeability, and induction of immune response by the host animal.

The microencapsulation technique that had previously met with the most success is that of O'Shea and Sun (1986) Diabetes, 35:943–946. Their method uses the strong interaction between large multicharged molecules, one cationic and one anionic, to form a very thin, stable, spherical membrane shell that resists the diffusion of large proteins, such as antibodies, while allowing the diffusion of smaller proteins, such as insulin.

Such a membrane is obtained by suspending cells to be encapsulated in a solution of algin, a polyanionic polysaccharide that is obtained from kelp. Very small droplets of this solution are formed, approximately 0.1–1.0 mm in diameter depending on the size of the material to be encapsulated, and these droplets are gelled on contact with a fairly highly concentrated solution of calcium chloride, 0.2–1.6% $CaCl_2$. The calcium cations, in this high concentration, serve to reversibly crosslink the anionic polysaccharide chains, forming the gel.

To obtain a membrane that would be stable at physiologic concentrations of calcium, the negatively charged microcapsule is placed in a solution of a positively charged polymer, for example, polylysine. The opposite charges interact, leading to very strong adsorption of the polylysine, resulting in a stable, strongly crosslinked surface. Similarly, an outer layer of algin is added, yielding an algin-polylysine-algin composite trilayer membrane.

The solid inner core of gelled algin is liquefied by placing the microcapsules in a solution of sodium citrate to chelate the gelling calcium. At physiologic calcium levels, the core remains liquid and the algin, if of low enough molecular weight, diffuses out of the core. The result is a spherical shell of algin-polylysine-algin surrounding the microencapsulated cells.

It is predictable that such an algin-polylysine-algin microcapsule will not resist tissue overgrowth. The exterior surface is highly charged, with both positive and negative charges, and would thus be expected to adsorb significant amounts of protein and to support cell adhesion. Andrade et al. (1986) Adv. Polymer Sci., 79:1–63. Experimentally, tissue overgrowth has been observed to be the point of failure of the microencapsulation therapy. O'Shea and Sun (1986).

Poly(ethyleneoxide) (PEO) has been used in numerous instances to decrease cellular attachment. For instance, PEO coatings on PVC tubes have been reported as significantly reducing platelet adhesion in vitro and preventing adhesion and thrombus formation in 72 day PVC tube implants in vivo. (Y. Mori et. al., Trans. Am. Soc. Artif. Intern. Organs 28:459 (1982)). Volume restriction and osmotic repulsion effects were credited with producing the low adsorption of blood constituents. (Id.). Later research concluded that there were micro flows of water induced by the cilia-like movements of hydrated PEO chains which prevent plasma proteins from absorbing onto the surface of coated PVC tubes. (S. Nagaoka and A. Nakao, Biomaterials 11:119 (1990)).

In addition to PVC tube coatings, others have reported that segmented polyurethanes containing PEO as the soft segment, when cast as films or coatings, show reduced platelet retention in vitro. (E. W. Merrill et al., Trans. Am. Soc. Artif. Intern. Organs 28:482 (1982)). PEG-polyurethane coatings on disks made of Pellethane were shown to cause the disks to have reduced cellular adhesion for up to 3 months when implanted into the peritoneal cavities of mice. (S. K. Hunter et al., Trans. Am. Soc. Artif. Intern. Organs 29:250 (1983)). Block co-polymers consisting of poly(N-acetylethyleneimine) and PEO, when coated on solids such as glass beads or silica, were found to increase the homeo-compatibility of the solids by decreasing adsorption of hydrophilic macromolecules. (C. Maechling-Strasser et al., J. of Biomedical Materials Research 23:1385 (1989)).

Long term canine vascular implants of Biomer coated with polymers have been tested for adsorption of proteins. (C. Nojiri et al. Trans. Am. So. Artif. Intern. Organs, 35:357 (1989)). The polymer coatings found to have "excellent non-thrombogenic performance" were: 1) Heparin immobilized on Biomer using a long chain PEO spacer; and 2) a block copolymer composed of 2-hydroxyethyl methacrylate (HEMA) and styrene. (Id.).

Low density polyethylene (a hydrophobic polymer surface) coated with a block copolymer containing water insoluble components (such as polypropylene oxide or polybutylene oxide) and PEO components (water soluble components) was shown to have protein resistant properties. (J. H. Lee et al., J. of Biomedical Materials Research, 23:351 (1989)). The surface was created by a simple coating process where the hydrophobic components of the polymer adsorbed on the hydrophobic surface of the polyethylene from an aqueous solution, the PEO chains were then at least partially extended into the aqueous solution creating a protein resistant surface. (Id.).

Processes used to achieve PEO surfaces other than a simple coating process have been described: block co-polymerization (Y. Mori supra); incorporation into polyurethanes (E. W. Merrill supra); and direct attachment of PEO molecules to the cyanuric chloride activated surface of a poly(ethylene terephthalate) film. (W. R. Gombotz et al., J. of Applied Polymer Science 37:91 (1989)).

Most of the foregoing uses of PEO have been on concave or flat surfaces; they have not been on small convex surfaces such as are found with microcapsules. Due to the fact that the non-ionic water soluble polymers face outward from the microcapsule, it could not be predicted from the prior art that PEO and other non-ionic water soluble polymers could form a sufficient barrier to protect microcapsular surfaces. Likewise, the chemistry was not known for attaching sufficient quantities of water soluble non-ionic polymers to the outer surfaces of microcapsules to create this barrier.

SUMMARY OF THE INVENTION

This invention for the first time demonstrates the use of water soluble non-ionic polymers such as PEO to create resistance to cell adhesion on the surface of microcapsules.

This invention provides a method for transplanting foreign material into an animal body in a biocompatible manner. This is accomplished by providing microcapsules, biocompatible with the recipient animal, capable of encapsulating the foreign material to be transplanted into that animal. The normally charged outer layer of the microcapsules is covered by water soluble non-ionic polymers such as poly(ethylene oxide) (PEO) which act to shield the charge. These polymers are grafted to the polycationic polymers, such as poly-L-lysine (PLL) molecules used as at least one of the layers of the microcapsule, such that they create a non-ionic barrier between the outer layer of the microcapsule (made of essentially either polycationic polymers, such as PLL, or polyanionic polymers, such as alginate) and the recipient animal. The microcapsules then appear, from the outside, to have water-like surface properties, thus reducing the driving force for protein adsorption. Further, the surface, at the macromolecular level, is in a high degree of motion, further reducing protein adsorption and cell attachment.

This invention further provides microcapsules, and a method for their production, in which the surface is more resistant to cell adhesion. As a result, overgrowth of the microcapsules by cells such as fibroblasts and macrophages is severely decreased or eliminated. Cells contained within the microcapsules are able to continue to receive nutrients and signal molecules, and produce whatever is their desired product. Any product present in the microcapsules, such as insulin produced by islet cells, can continue to diffuse out of the microcapsules and be available for utilization by the host animal.

This invention also provides microcapsules, and a method for their production, which will not appreciably stimulate immune response or cytokine release by the recipient animal. Thus, these microcapsules can be transplanted to a recipient animal and function there with minimal interference from that animal's immune system.

This invention provides microcapsules with variable levels of permeability. This is accomplished by using varying numbers of layers to make the microcapsules, with an increased number of layers decreasing the pore size. Thus, the microcapsules can be created to meet a particular need for large or small pores and the resulting level of permeability.

BRIEF DESCRIPTION OF THE DRAWINGS

FIGURES

Figure 1:
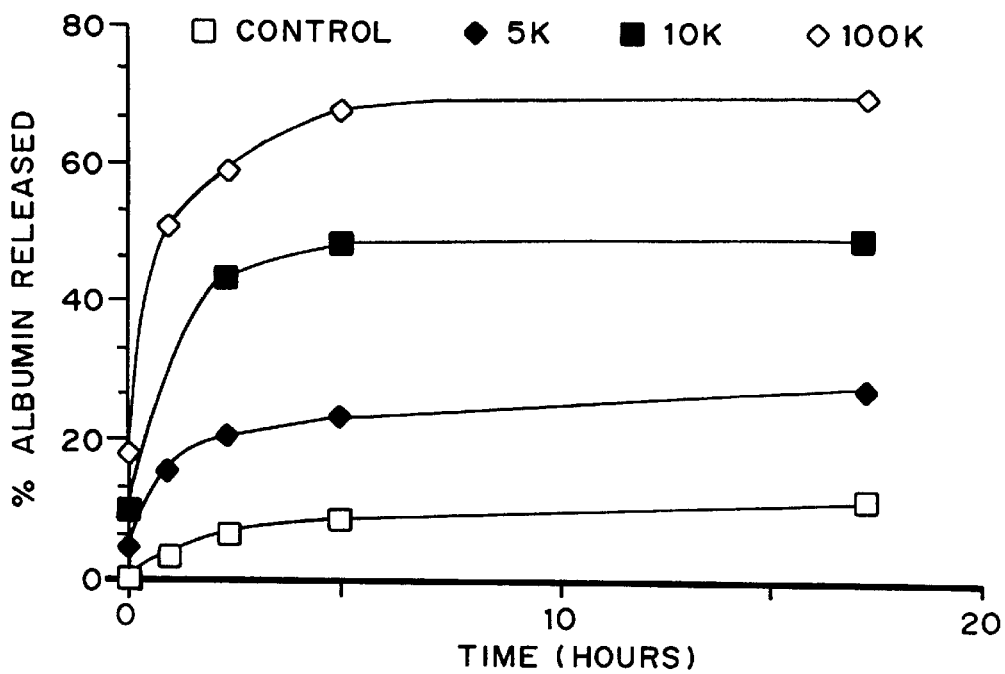

FIG. 1 shows the effect of the molecular weight of the water soluble non-ionic polymer on permeability of microspheres formed using grafted material.

Figure 2:
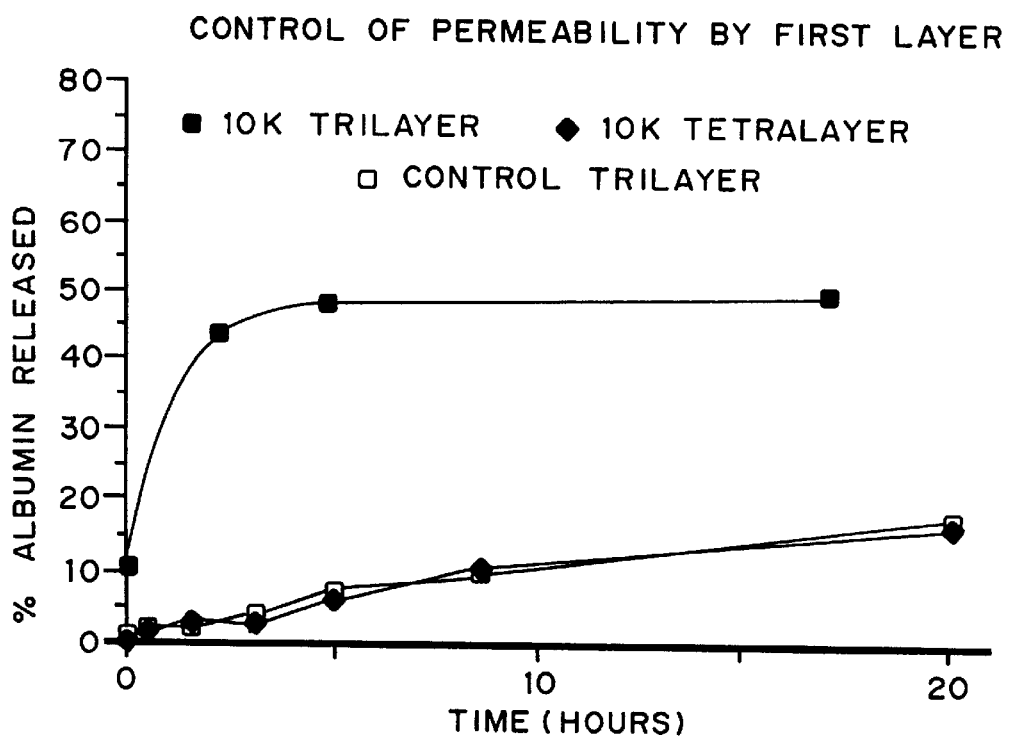

FIG. 2 shows the effect of the number of layers used to form the microspheres on permeability.

Figure 3:
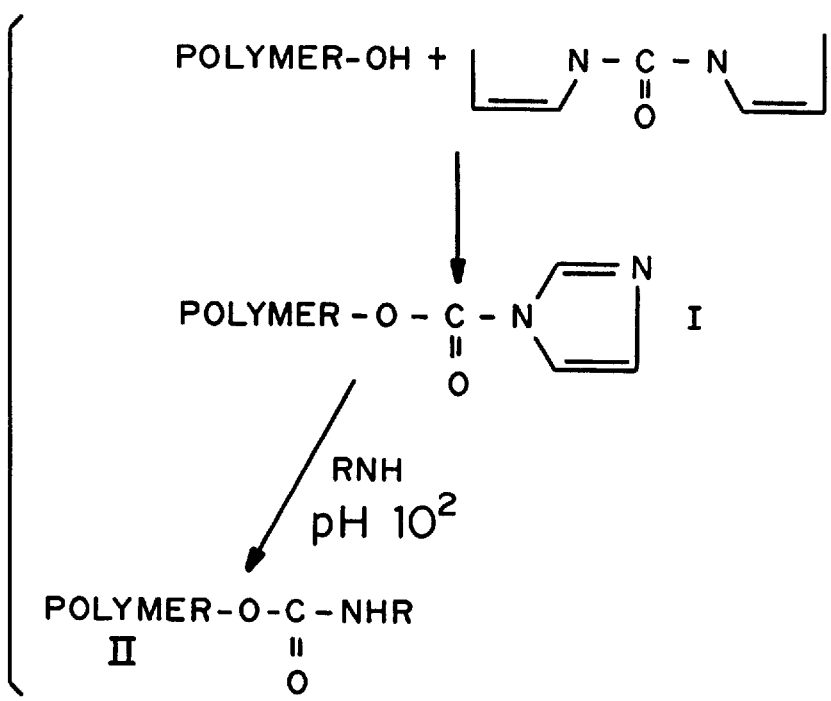

FIG. 3 is a schematic of the activation reaction using carbodiimidazole.

Figure 4:
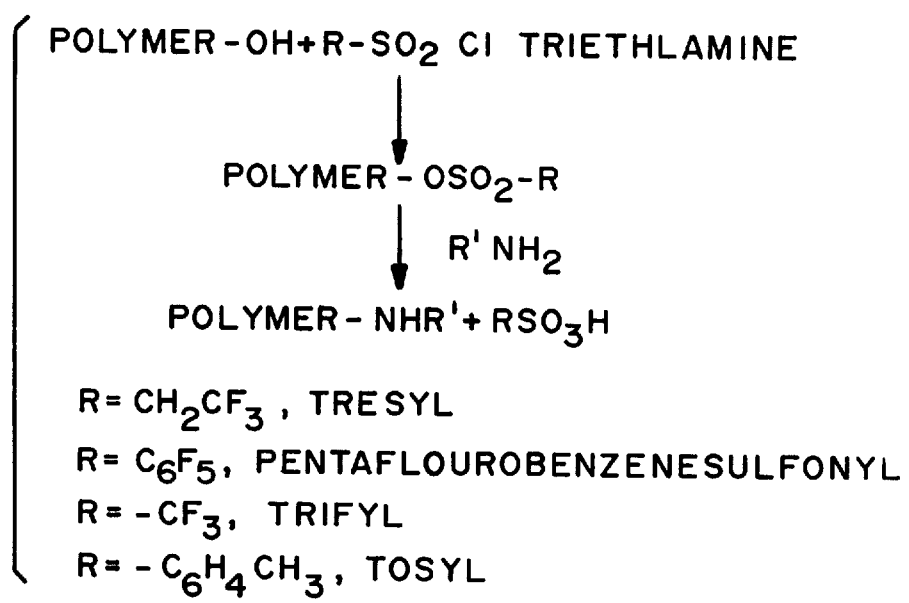

FIG. 4 is a schematic of the activation reaction using sulfonyl chlorides, where R is as shown.

Figure 5A:
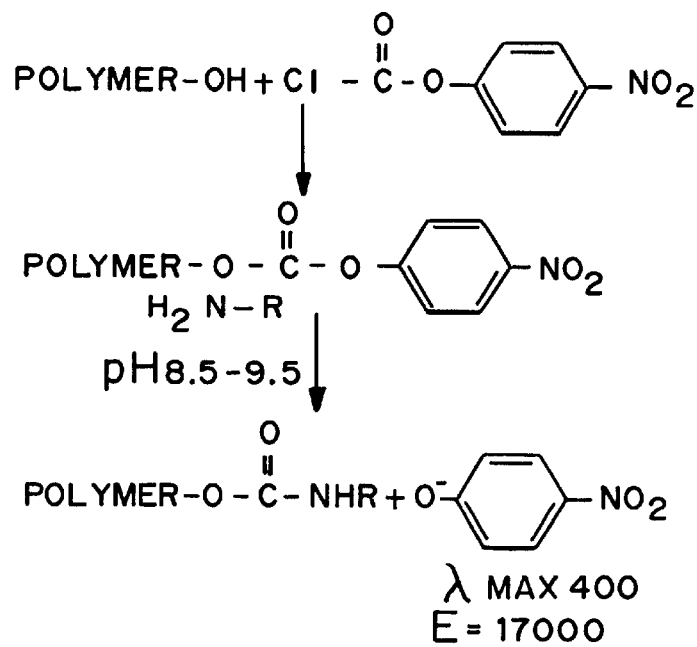
Figure 5B:
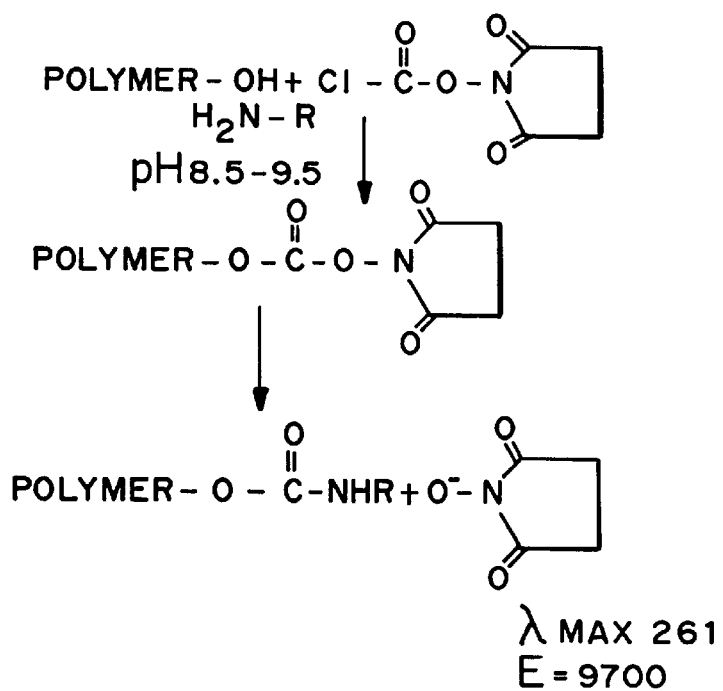
Figure 5C:
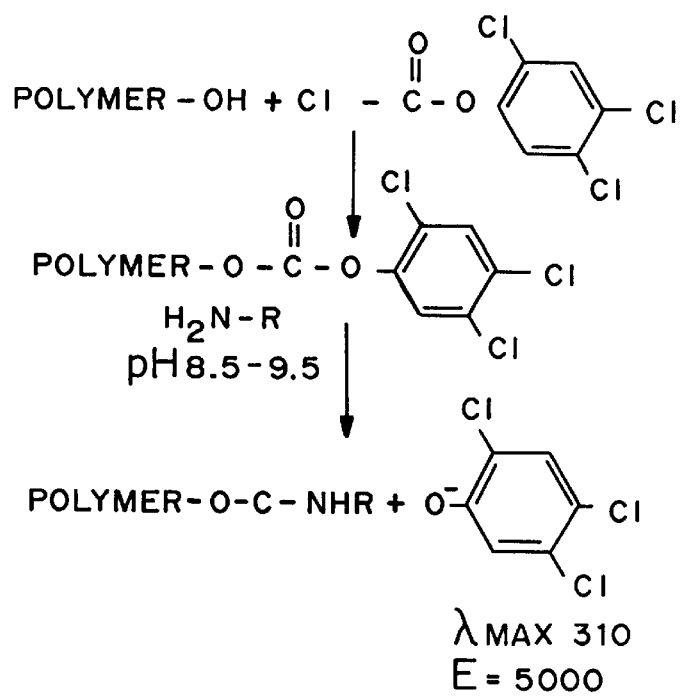

FIG. 5 is a schematic of the activation reaction using chlorocarbonates.

Figure 6A:
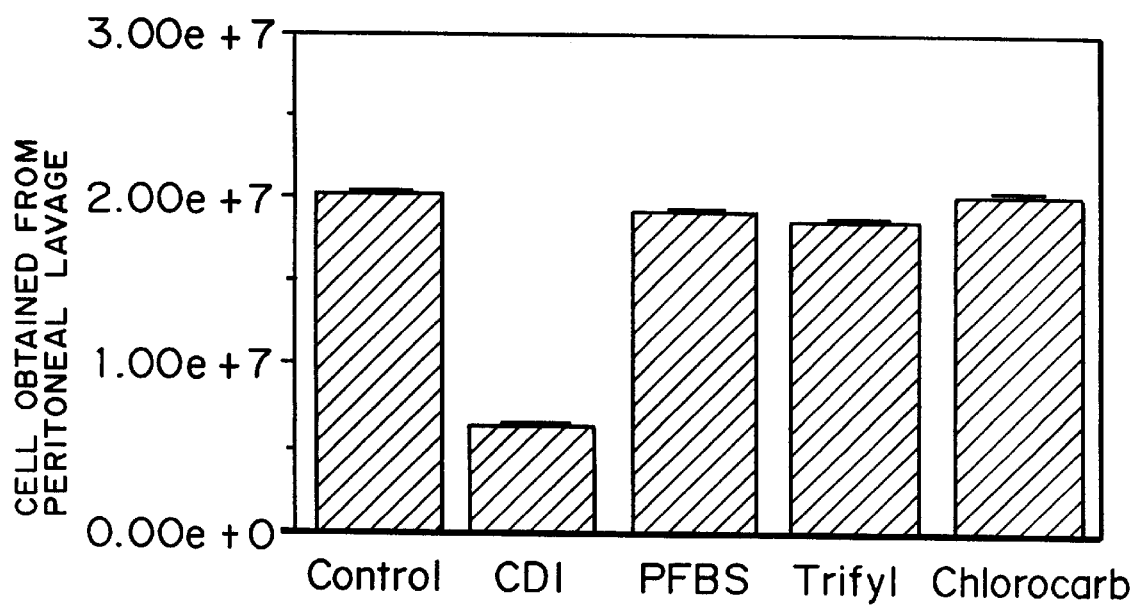
Figure 6B:
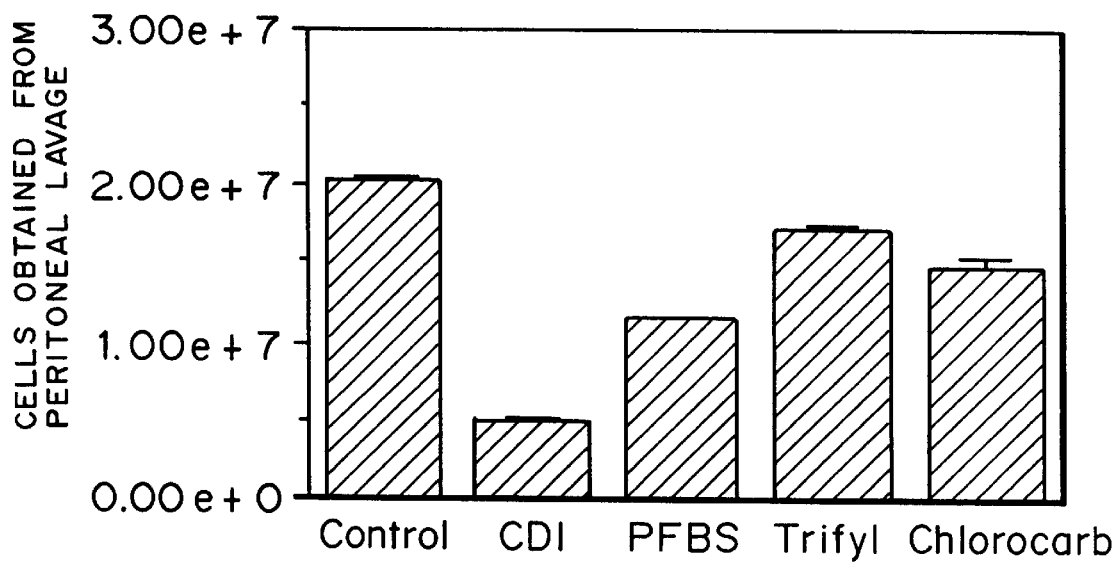
Figure 6C:
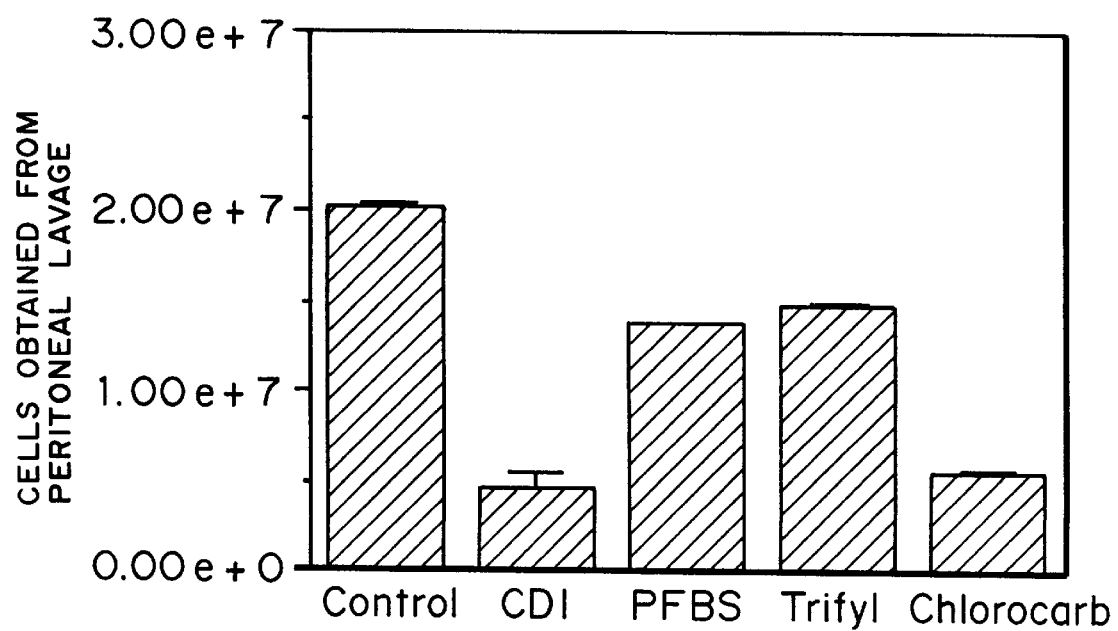

FIG. 6 shows cell counts obtained from peritoneal lavage after implantation of microcapsules. CDI (carbodiimidazole), PFBS (pentafluorobenzenesulfonyl chloride), trifyl (trifyl chloride), and chlorocarb (chlorocarbonate) were used to activate PEO (poly(ethylene oxide)) for grafting to poly(l-lysine) according to this invention. FIG. 6a represents results when PEO of molecular weight around 5 kd was used; FIG. 6b used PEO of 10 kd; and FIG. 6c shows results from PEO of 18.5 kd. Numbers of cells are shown on the left of each graft. e+7 stands for $10^7$, so that 1.00 e+7 is $1.00 \times 10^7$ cells.

DETAILED DESCRIPTION

According to this invention, microcapsules are assembled from various layers of a polyanionic polysaccharide, such as alginate, and a polycationic polymer, such as poly(l-lysine) (PLL). The polycationic polymer need not be a polypeptide. The outer polycation layer is composed of the polycationic polymer grafted to a water soluble non-ionic polymer, such as poly(ethylene oxide) (PEO) to form a graft copolymer, such as PLL-g-PEO. The layers are alternated such that the oppositely charged polymers, for example algin and PLL, aggregate to form coacervates, such as algin--PLL--algin. This creates an ionically crosslinked membrane.

However, PLL is known to promote cell adhesion, so at least the outermost layer of PLL or other polycation in this invention is composed of the graft copolymer. PEO, as well as other water soluble non-ionic polymers, have been shown to reduce cell adhesion when used to modify a surface. Lee et al. (1989) J. Biomed. Materials Res. 23:351–368. This dual-character graft copolymer interacts with the polyanionic layer, such as algin, to form a stable membrane through interactions between the polycationic backbone, such as PLL, and the polyanionic layer. The long arms of the non-ionic polymer, such as PEO, however, serve to obscure the charged layers from the tissues, thereby improving the biocompatibility. They create a very hydrophilic and uncharged layer, to which very little, if any, protein or cells adhere.

The water soluble non-ionic polymers are covalently attached to the polycationic polymers and point in all directions including outward from the microcapsule.

1. Water Soluble Non-ionic Polymers

Water soluble non-ionic polymers with molecular weights of between 2000 and 50,000 are suitable for this procedure. PEO of approximately 10,000 m.w. is the most preferred. Molecules with molecular weights lower than around 2000 do not adequately shield the microcapsule, while those greater than around 50,000 create steric limitations on the microcapsules. In addition, molecules with higher molecular weights cause an increase in the swelling of the microcapsules, interfering with the interactions between the polyanionic polysaccharides and the polycationic polypeptides. As a result, the polyanionic polysaccharide layer does not adhere as well, and the integrity of the microcapsules can be threatened.

Additionally, the size of the water soluble non-ionic polymers affects permeability of the microcapsule. The larger molecules create greater permeability. This feature can be manipulated to obtain the optimal degree of permeability for the particular use of the microcapsules. For microcapsules encapsulating insulin-producing islet cells, the optimal permeability is created with PEO around 10,000 m.w. in a pentalayer membrane (see below and FIGS. 1 and 2).

2. Activation

Procedures used to graft the water soluble non-ionic polymers to the polycationic polymers include but are not limited to use of carbodiimidazole, sulfonyl chlorides, or chlorocarbonates to activate the water soluble non-ionic polymers. These reagents are used to activate free hydroxyl groups for coupling to polycationic polypeptides.

Other chemistries for linking water soluble non-ionic polymers to polycationic polymers, known by those skilled in the art, can also be used.

a. Carbodiimidazole

To X millimoles of PEO or other water soluble nonionic polymer in at least a 1% solution in anhydrous acetone or other anhydrous organic solvent is added at least 1X, preferably 5X millimoles of carbodiimidazole. Larger quantities of carbodiimidazole can be used but will not increase the rate or amount of the activation. The reaction mixture is stirred at a temperature above the freezing point and below the melting point of the mixture, preferably at room temperature of around 22° C., for at least ½ hour, preferably around 2 hours. The product is then washed at least twice with methanol with HCl or other strong acid to convert the organic base to the conjugate, and finally with pure methanol. Washes can be formed by solubilization of the reaction product in the wash solvent, followed by reprecipitation and sedimentation, for example by settling at 1 g or in a centrifuge at higher acceleration, preferably 1000 rcf for 10 minutes. The final wash is checked to be free of any residual pyridine or other base by UV spectrophotometry. The pelleted product is then recovered. Other purification schemes known by those skilled in the art can also be used. The product can then be lyophilized and stored. FIG. 1 shows the reaction scheme.

b. Sulfonyl chlorides

To create good leaving group characteristics in sulfonyl chlorides, two main approaches are used: the first is fluorination and the second is nitration. Thus a number of organic chlorides can be used to produce end-activated water soluble non-ionic polymer chains with a varying degree of effectiveness. By way of example, the order of reactivity of coupling for Toluene sulfonyl chloride (Tosyl chloride): Trifluoroethanesulfonyl chloride (Tresyl chloride): Trifluoromethanesulfonyl chloride (Trifyl chloride) is 1:100:4000. As reactivity increases, stability decreases. Therefore an organic chloride with intermediate traits is preferred. Other sulfonyl chlorides such as dansyl, dipsyl, and diabsyl chloride can also be used, but with lower effectiveness. Other problems such as difficulty in removal of unreacted dansyl functions by nucleophiles and tendency for diabsyl chloride to undergo further secondary reactions leading to a significant red shift make these sulfonyl chlorides less suitable. These may be overcome, for example, by employing higher levels of the activating agent and subsequently purifying the products of the primary reaction from the products of the secondary competing reactions.

Another compound, Pentafluorobenzenesulfonyl chloride (PFBS), however, is as reactive as tresyl chloride, is cheaper, and is chromophoric, thus allowing an easy quantification of the extent of the reaction. Thus PFBS is a preferred reagent in this group.

Sulfonyl chlorides are readily available from a number of commercial chemical suppliers such as Aldrich and Fluka.

To X millimoles of PEO or other nonionic water soluble polymer in at least a 1% solution in anhydrous methylene chloride or other anhydrous organic solvent at a temperature above the freezing point and below the melting point of the mixture, preferably 4° C., is added at least 1X, preferably 5X millimoles of sulfonyl chloride (larger quantities can be used but will not increase the rate or amount of the activation) and approximately twice as much pyridine, triethylamine, or other organic aprotic base, as sulfonyl chloride. The reaction mixture is stirred for at least 10 minutes, preferably around 2 hours. The product is then washed at least twice with methanol with HCl or other strong acid to convert the organic base to the conjugate, and finally with pure methanol. Washes can be formed by solubilization of the reaction product in the wash solvent, followed by reprecipitation and sedimentation, for example by settling at 1 g or in a centrifuge at higher acceleration, preferably 1000 rcf for 10 minutes. The final wash is checked to be free of any residual pyridine or other base by UV spectrophotometry. The pelleted product is then recovered. Other purification schemes known by those skilled in the art can also be used. The product can then be lyophilized and stored. FIG. 2 shows the reaction scheme.

c. Chlorocarbonates

Chlorocarbonates such as P-nitrophenyl chlorocarbonate (Fluka), 2,4,5 trichlorophenyl chlorocarbonate, and N-hydroxysuccinamide chlorocarbonate are examples that react efficiently for activation of hydroxyl containing compounds such as the water soluble non-ionic polymers used in this invention. Other chlorocarbonates known by those skilled in the art can also be used.

To X millimoles of PEO or other water soluble nonionic polymer in at least a 1% solution in anhydrous methylene chloride or other anhydrous organic solvent at a temperature above the freezing point and below the melting point of the mixture, preferably 4° C., is added at least 1X, preferably 5X millimoles of chlorocarbonate (larger quantities can be used but will not increase the rate or amount of the activation) and approximately twice as much pyridine, triethyl amine or other organic aprotic base. The reaction mixture is stirred at a temperature above the freezing point and below the melting point of the mixture, preferably at room temperature of around 22° C., for at least 10 minutes, preferably around 2 hours. The product is then washed at least twice with methanol with HCl or other strong acid to convert the organic base to the conjugate, and finally with pure methanol. Washes can be performed by solubilization of the reaction product in the wash solvent, followed by reprecipitation and sedimentation, for example by settling at 1 g or in a centrifuge at higher acceleration, preferably 1000 rcf for 10 minutes. The final wash is checked to be free of any residual pyridine or other base by UV spectrophotometry. The pelleted product is then recovered. Other purification schemes known by those skilled in the art can also be used. The product can then be lyophilized and stored. FIG. 3 shows the reaction schemes.

3. Polycationic Polymers

Polycationic polymers are selected for their ability to form strong membrane coacervates with algin or other polyanions. Such polycationic polymers include polypeptides and non-polypeptides. Polypeptides include, but are not limited to, polylysine and polyornithine. Non-polypeptides include, but are not limited to, polyethyleneimine and polyallylamine. The molecular weight of these polycationic polymers is important but not critical, and optimal values are determined by their ability to form strong membrane coacervates. Very low molecular weight polycation polymers generally form membranes that are weak and very high polycation polymers generally form membrane coacervates that are very thin. Typical values for the molecular weight of the polycation polymers are between about 10,000 and 75,000. A preferred substrate is poly(l-lysine), which has been previously used in its ungrafted form as a component of microcapsule membranes.

4. Coupling

Activated water soluble non-ionic polymers are next coupled to the polycationic polymers. The polymers are mixed into a solution of the activated PEO or other water soluble nonionic polymer, agitated and allowed to react for a period of at least ½ day. The pH of the solution is maintained around 9±2. The coupling reaction is stopped by quenching through the addition of an amine or a thiol such as mercaptoethanol. Quenching is allowed to proceed for at least ½ hour, preferably 10 hours.

If desired, ultrafiltration, dialysis, or Soxlet extraction can be used to separate the unreacted PEO from the PLL-g-PEO. In addition, the extent of reaction can be estimated using a spectrophotometric titration of amine groups where, for example, the amine groups are reacted with 2,4,6-trinitrobenzene sulfonic acid, forming a product that absorbs at 440 nm. The extent of reaction can also be determined by estimating the relative amounts of copolymers using $^1$H-NMR.

5. Formation of Microcapsules

Formation of the microcapsule is by standard techniques. O'Shea and Sun (1986). Material to be encapsulated is suspended in a solution of polyanionic polysaccharides, preferably algin, at a concentration that will allow the cells to receive adequate nutrients as well as signal molecules and produce the desired product(s) once the microcapsules are formed. A preferred concentration is $1 \times 10^5$ to $1 \times 10^8$ cells/ml. Droplets of this solution are dropped into a solution of isotonic calcium chloride in saline, preferably 0.2 to 1.6% $CaCl_2 \cdot 2H_2O$. Passing the solution under pressure through a fine-gauge needle or orifice in a sterile air stream is one method of producing the droplets. They are then washed in isotonic saline or buffer and placed in a solution of the polycationic polymer, preferably PLL. Alternatively, they can be placed in a solution of water soluble non-ionic polymer-grafted-polycationic polymer, as described herein. The polycationic polymer or water soluble non-ionic polymer-grafted-polycationic polymer solution should be approximately 0.03%–0.3%, preferably 0.1%. The droplets are allowed to react with the polymers for a period of time from 3–30 minutes, preferably 12 minutes.

The microcapsules are removed from the polymer solution by, for example, decanting the liquid. The 2-layer droplets are then washed with isotonic saline or buffer and may be coated with one or more layer of polyanionic polysaccharides, preferably another layer of algin. This is accomplished by reacting the bilayer droplets with a 0.05–0.25% solution of polyanionic polysaccharide, preferably a 0.15% solution of algin, for a period of 3–30 minutes, preferably 8 minutes.

Next, a layer of water soluble non-ionic polymer-grafted-polycationic polymer, preferably PEO-g-PLL, can be added to the microcapsule. This is performed by incubation of the microcapsules in a solution of the grafted polymer at the same concentration range, for the same period of time, as for the non-grafted polycationic polymers. Alternatively, the first layer of polycationic polymer may be replaced by water soluble non-ionic polymer-grafted-polycationic polymer, such as PLL-g-PEO, and the second layer of this grafted-polycationic polymer may be included or omitted. An outer layer of algin may or may not be added at the same concentration range, for the same period of time, as for the inner one.

The number of layers used in each microcapsule can be used to determine several parameters of interest for transplantation. The prior art discloses use of microcapsules with 3 layers, as described in O'Shea and Sun (1986). The number of layers can be increased by adding subsequent alternating layers of polyanionic polysaccharides and polycationic polypeptides. The polycationic polymers grafted to the water soluble non-ionic polymers should at least be used as the last or next to last layer of the microcapsule, and must be at least the outermost polycationic layer.

Increasing the number of layers decreases the permeability of the microcapsules. Thus, permeability can be controlled to selectively allow diffusion across the microcapsule membrane. The addition of water soluble non-ionic polymers to the polycationic polypeptide layer increases permeability. Therefore, in order to eliminate the immune response of the host animal to cells encapsulated within these microcapsules, such as xenograft insulin producing islet cells, it is necessary to counter this permeability increase. A preferred method is to add an additional two layers to the surface of the microcapsule. This brings the permeability back to the level found in 3-layer microcapsules described in the art which do not have the grafted water soluble non-ionic polymers.

Additionally, increasing the number of layers of the microcapsule membrane increases the strength and stability of the microcapsules. However, this stability must be balanced with the decrease in permeability caused by the increased layers. Thus, for use in encapsulating living cells that produce a desired product when transplanted to a host animal, a 5-layer microcapsule according to this invention is most preferred, whether made with both ungrafted and grafted polycation polymer or solely with grafted polycation polymer.

Microcapsules formed by the above procedures can be degelled at this step to remove excess gelled polyanionic polysaccharide immediately surrounding the encapsulated material. However, this procedure is not a necessary step, and the microcapsules will function well without degelling. If degelling is desired, standard procedures described in the art, such as incubation in a sodium citrate solution can be employed. O'Shea and Sun (1986).

6. Implantation of Microcapsules

Microcapsules are suspended in a solution compatible for injection, such as isotonic saline, buffer or tissue culture medium. Microcapsules can be implanted in the peritoneal cavity of a host animal by standard techniques. In addition, they can be implanted in any bodily location which provides sufficient circulation of the products of the encapsulated material to allow metabolic functioning of those products. For example, with microcapsules containing insulin-producing islet cells, intramuscular locations will allow sufficient exposure to the blood circulatory system to allow effective use of the insulin.

EXAMPLE 1

Activation of PEO Using Carbodiimidazole

Three separate reactions were performed, each using PEO of a different molecular weight class. 1 millimole each of PEO-5K (5000 d), PEO-10K (10,000 d) and PEO-18.5K (18,500 d) were used. The PEO-5K material was monomethoxy end terminated; as such these polymers had only one terminal, activatable hydroxyl group, thus minimizing cross-linking reactions in the coupling step. 50% solutions of these polymers were made up in anhydrous acetone which had been dried overnight over 4 Å molecular sieves, and 5 millimoles of carbodiimidazole (CDI) was added to them. The reaction mixes were stirred at room temperature for 2 hrs. The reaction mixes were then washed four times with 60 ml of anhydrous acetone by chilling the solution to 0° C. to precipitate, decanting, adding fresh solvent, and warming to 22° C. to redissolve. The product was then lyophilized and stored.

EXAMPLE 2

Activation of PEO Using Sulfonyl Chlorides

Three separate reactions were performed, each using PEO of a different molecular weight class. 1 millimole each of PEO-5K, PEO-10K AND PEO-18.5K were used. The PEO-5K material was monomethoxy end terminated; as such these polymers had only one terminal, activatable hydroxyl group, thus minimizing cross-linking reactions in the coupling step. 50% weight/volume solutions of these polymers were made up in anhydrous acetone which had been dried overnight over 4 Å molecular sieves. The solutions were cooled to 4° C. and 5 millimoles of trifyl chloride or PFBS was added to these solutions along with 10 millimoles of pyridine. The reaction mix was stirred mechanically at room temperature for 2 hrs., at the end of which it was washed twice with 60 ml each of methanol containing 0.2 ml concentrated HCl, three times with 60 ml each of methanol containing 50 $\mu$l of HCl, and finally with pure methanol. The washes were done by solubilization at 40° C. and precipitation at 4° C. followed by centrifugation at 1000 rcf. The final wash was checked to be free of any residual pyridine by ultraviolet spectroscopy. The product was lyophilized and stored at 4° C.

EXAMPLE 3

Activation of PEO Using P-Nitrophenyl Chlorocarbonate

Three separate reactions were performed, each using PEO of a different molecular weight class. 1 millimole each of PEO-5K, PEO-10K AND PEO-18.5K were used. The PEO-5K material was monomethoxy end terminated; as such these polymers had only one terminal, activatable hydroxyl group, thus minimizing cross-linking reactions in the coupling step. 50% solutions of these polymers were made up in acetone which had been dried overnight over 4 Å molecular sieves. The solutions were then cooled to 4° C. and 5 millimoles each of pyridine and triethylamine and 5 millimoles of p-nitrophenyl chlorocarbonate (chlorocarb) were added. The mixtures were mechanically stirred and the reaction was allowed to proceed at room temperature for 2 hrs. The reaction mix was then washed with cold acetone by adding 60 ml acetone at room temperature, cooling to 4° C. and centrifuging at 1000 rcf. The washing was repeated once with acetone, then with a 5% acetic acid solution in dioxane, and finally with methanol. The product was lyophilized and stored.

EXAMPLE 4

Coupling Activated PEO to PLL 20 mg of Poly(l-lysine) (PLL), molecular weight around 17,000, was added to each 50% w/v solution of the above activated polymers in 500 mM sodium borate buffer (pH 9) for 24 hours. The coupling reaction was stopped by quenching using 0.36 mls of 14M Mercaptoethanol. The quenching was allowed to proceed for 10 hrs.

The PEO-5K grafted to PLL and PEO-10K grafted to PLL formed clear solutions. On the other hand, the PEO-18.5K grafted to PLL resulted in the formation of a very high molecular weight macromolecular network which had the consistency of a gel. Some parts of this gel were soluble when diluted further but some crosslinked portions remained insoluble.

No attempt was made to separate the unreacted PEO from the PLL-g-PEC. The extent of reaction was estimated using spectrophotometric titration of amine groups where the amine groups were reacted with 2,4,6-trinitrobenzene sulfonic acid, forming a product that absorbs at 440 nm.

EXAMPLE 5

Relationship of Molecular Weight of the Water Soluble Non-Ionic Polymer to Permeability of Microspheres Use of grafted water soluble non-ionic polymer to polycationic polymer was found to affect the permeability of microcapsules. Microspheres were formed using PEO of varying molecular weights grafted to PLL as the outer layer of a bilayer microsphere. The relationship of the size of the PEO used to the permeability of the microspheres was investigated.

5 ml of algin solution was mixed with 100 µl of $^{125}I$ labelled BSA for microsphere fabrication. Microspheres were formed following standard procedures. PLL-g-PEO having PEO chains of 5,000 d, 10,000 d, and 100,000 d were used as the outer layer. Control spheres were formed having ungrafted PLL as the outer layer. The microspheres were degelled with citrate. The degelled microspheres were incubated in 10 ml of citrate solution, which was sampled periodically for presence of $^{125}I$ albumin that had secreted through the membrane. For this sampling, 1 ml aliquots were counted in a gamma scintillation counter. As can be seen in FIG. 1, permeability of the microspheres increased in direct proportion to the size of the PEO component of the outer layer, with control spheres having ungrafted PLL being the least permeable.

The effects of the presence of PEO on permeability could be reversed by increasing the number of layers used to form the microspheres. Following standard procedures, microspheres were formed having from two to four layers. As can be seen in FIG. 2, microcapsules with PEO having 4 layers, where the inner polycationic layer was of ungrafted PLL, had the same permeability characteristics as the control microcapsules with 3 layers. Thus, varying the number of layers altered the permeability characteristics of the microspheres, and increasing the number of layers, using an inner layer of ungrafted PLL, returned the microcapsules to their original permeability, based on the standard microcapsule.

EXAMPLE 6

Implantation

Approximately 0.5 ml of microcapsules were taken for each sample. The samples were washed 2 times in 10 ml each of isotonic saline. After the final wash, each sample of microcapsules was suspended in 5 ml phosphate buffered saline (0.2M) pH 7.4 (PBS) and aliquoted into two equal parts. Duplicate animals, male swiss Sprague-Dawley mice 16–20 weeks old were used for each composition. Implants were made intraperitoneally (i.p.) using a 15 gauge needle. Animals were under ether anaesthesia. Microcapsules having an outermost layer of PLL without the grafted water soluble non-ionic polymers were used as controls.

EXAMPLE 7

Characterization of Implanted Microcapsules

The implants were retrieved after one week using peritoneal lavage. 5 ml of PBS, containing 10 U/ml heparin, was injected with pressure using a 22 gauge needle. The microcapsules were recovered using a transfer pipette through a small hole made in the muscle flap over the peritoneal cavity.

a) Cell Counts

An immediate count of free cells recovered in the fluid in conjunction with the microcapsules was taken. These cells were incubated in polystyrene petri dishes for 2 hrs and then washed and fixed in 2% glutaraldehyde. Those cells adhering to the petri dish were nearly uniformly found to be macrophages as revealed using a monoclonal antibody and secondary fluorescence technique. The primary antibody was a rat anti-mouse macrophage antibody, clone #Ml-70.15 from Sera-lab obtained from Accurate Chemicals. The secondary antibody was a fluorescein conjugated goat anti-rat IgG polyclonal antibody obtained from Accurate Chemical. After antibody treatment, the samples were viewed by fluorescence microscopy. Some of the directly recovered peritoneal lavage fluid and some control microcapsules which were covered with cells were also treated using the antibody fluorescence technique and were qualitatively judged to be about 50% macrophages.

The results, shown in FIG. 4, show that the number of macrophages free floating in the peritoneal fluid was decreased by use of the products of this invention. This figure shows cell counts from the samples. As can be seen from this figure, use of the technology described in this invention lowers the number of macrophages and other cells induced by the presence of microcapsules in the peritoneal cavity. Evidence of some foreign body giant cell formation was seen in all samples that had cellular attachment. Varying levels of fluorescence was seen in some macrophages which might be an artifact of non-uniform staining or may reflect different levels of cellular activation. A few cells which were not macrophages were also seen but their numbers were small.

The number of cells present in the peritoneal cavity was inversely correlated to the molecular weight of the grafted PEO.

b) Photomicrographs

A number of photomicrographs of the recovered microcapsules were taken. Photographs for each type of microcapsule were taken through a 40X phase contrast and a 400X Hoffman optics microscope. The lower magnification was used to reflect a broad cross-section of the microcapsules and the higher magnification was used to examine the surface of the microcapsules and closely examine cell attachment.

The control microcapsules, prepared from ungrafted poly (l-lysine), showed heavy cellular overgrowth as expected. A number of microspheres were darkened by overgrowth of cells.

Microcapsules made according to the invention described herein showed little or no cell attachment. This can be seen by the clarity and transparency of the microcapsular surfaces at the 40X magnification. Additionally, at 400X magnification, surfaces of the microcapsules made using trifyl chloride and chlorocarbonate technology show clean surfaces.

We claim:

1. A biocompatible microcapsule for transplantation into an animal comprising a membrane of more than one layer, with an outermost layer of hydrophilic non-ionic water soluble polymers that have been covalently grafted to at least one of the layers, made of polyamine, polyamide or polyimine polycationic polymers able to form strong membrane coacervates of the microcapsule membrane, wherein the hydrophilic polymer is of an effective molecular weight to shield the microcapsules from cellular adhesion and provide an effective permeability to the microcapsules.

2. The microcapsule of claim 1 wherein the non-ionic water soluble polymers are selected from the group consisting of poly(ethylene oxide), poly(vinyl pyrrolidone), poly(ethyl oxazoline), poly(vinyl alcohol) and polysaccharides.

3. A biocompatible microcapsule for transplantation into an animal comprising a membrane of more than one layer, with an outermost layer of dextran that has been covalently grafted to at least one of the layers, made of polyamine, polyamide or polyimine polycationic polymers able to form strong membrane coacervates of the microcapsule membrane wherein the dextran is of an effective molecular weight to shield the microcapsules from cellular adhesion and provide an effective permeability to the microcapsules.

4. A biocompatible microcapsule for transplantation into an animal comprising a membrane of more than one layer, with an outermost layer of hyaluronic acid that has been covalently grafted to at least one of the layers, made of polyamine, polyamide or polyimine polycationic polymers able to form strong membrane coacervates of the microcapsule membrane, wherein the hyaluronic acid is of an effective molecular weight to shield the microcapsules from cellular adhesion and provide an effective permeability to the microcapsules.

5. The microcapsule of claim 2 wherein the water soluble non-ionic polymers are branched.

6. The microcapsule of claim 2 wherein the water soluble non-ionic polymers are unbranched.

7. The microcapsule of claim 1 wherein the polycationic polymers are selected from the group consisting of polylysine, polyornithine, polyethyleneimine, polyallylamine, and mixed copolymers thereof.

8. A biocompatible microcapsule for transplantations into an animal comprising a membrane of more than one layer, with an outermost layer of hydrophilic non-ionic water soluble polymers selected from the group consisting of poly(ethylene oxide), poly(vinyl pyrrolidone), poly(ethyl oxazoline), poly(vinyl alcohol) and polysaccharides, or copolymers thereof, that have been covalently grafted to at least one of the other layers, made of polyamine, polyamide or polyimine polycationic polymers selected from the group consisting of polycationic polyamino acids, polyethyleneimine and polyallylamine, or copolymers thereof, of the microcapsule membrane, wherein the hydrophilic polymer is of an effective molecular weight to shield the microcapsules from cellular adhesion and provide an effective permeability to the microcapsules.

9. The microcapsule of claim 8 wherein the polycationic polyamino acids are selected from the group consisting of polylysine, polyornithine, and copolymers thereof.

10. An improved biocompatible microcapsule for transplantation into an animal, having improved resistance to overgrowth by cells, comprising a membrane of more than one layer, characterized in that the outermost layer comprises exposed non-ionic chains of a graft copolymer, the graft copolymer comprising at least one block of a polycationic polymer and at least one block of a hydrophilic, water soluble, non-ionic polymer, and the graft copolymer adhered to the microcapsule predominantly by ionic bonds, wherein the hydrophilic polymer is of an effective molecular weight to shield the microcapsules from cellular adhesion and provide an effective permeability to the microcapsules.

* * * * *